United States Patent [19]

Agnes et al.

[11] Patent Number: 5,095,153
[45] Date of Patent: Mar. 10, 1992

[54] DIETHERS USABLE IN THE PREPARATION OF ZIEGLER-NATTA CATALYSTS

[75] Inventors: Giovanni Agnes; Giampietro Borsotti, both of Novara; Giuliana Schimperna, Milan; Elisabetta Barbassa, Pavia, all of Italy

[73] Assignee: HIMONT Incorporated, Wilmington, Del.

[21] Appl. No.: 595,529

[22] Filed: Oct. 11, 1990

Related U.S. Application Data

[63] Continuation-in-part of Ser. No. 413,409, Sep. 27, 1989, abandoned.

Foreign Application Priority Data

Sep. 30, 1988 [IT] Italy .................. 22152 A/88

[51] Int. Cl.$^5$ .................. C07C 43/115; C07C 43/18; C07C 43/20
[52] U.S. Cl. .................. 568/660; 568/609; 568/611; 568/641; 568/648; 568/662; 568/670; 568/672
[58] Field of Search ............ 568/644, 659, 670, 660, 568/607, 608, 609, 613, 611, 641, 648, 662, 664, 672, 671

[56] References Cited

U.S. PATENT DOCUMENTS 4,374,282  2/1983  Maldonado et al. .................. 568/672

OTHER PUBLICATIONS

Leboida et al., Chem. Abstracts, vol. 91, pp. 634, 1979.
Matsuzaki, K., et al., "Nuclear Magnetic Resonance Stuides on Poly(alkyl propenyl ether) and Model Compounds, 1, Conformational Analysis of Model Compounds", Macromolecules, vol. 14, pp. 1004–1008, 1981.
Whalon, Michael R., et al., "A Remarkable Consistency in Conformational Preference for a Series of 1,3-Disubstituted-2,2-Dimethylpropanes", Tetrahedron Letters, vol. 23, No. 50, pp. 5247–5250, 1982.
McAlees, Alan J., et al., "Complexes of Titanium Tetrachloride with Terdenate Tripod Ligands, Competition among Oxygen, Sulfur, and Nitrogen for Coordination Sites on Titanium", Inorganic Chemistry, vol. 15, pp. 1065–1074, 1976.

Primary Examiner—Marianne Cintins
Assistant Examiner—Margaret Argo

[57] ABSTRACT

Diethers of general formula:

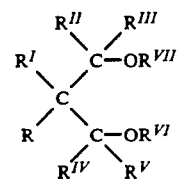

where R, $R^I$, $R^{II}$, $R^{III}$, $R^{IV}$ and $R^V$ are the same or different and are H, $C_{1-18}$ linear or branched alkyl, $C_{5-18}$ cycloalkyl, $C_6$–aryl, $C_{7-18}$ alkylaryl or $C_{7-18}$ arylalkyl radicals, provided that when R is alkyl, $R^I$ is other than H or alkyl and when $R^I$ is alkyl, R is other than H or alkyl; $R^{VI}$ and $R^{VIII}$ are the same or different and are $C_{1-18}$ linear or branched alkyl, $C_{5-18}$ cycloalkyl, $C_{6-18}$ aryl, or $C_{7-18}$ arylalkyl radicals; and two or more of R to $R^V$ may be bonded to form a cyclic structure having 5 to 18 carbon atoms.

The diethers are particularly useful in the preparation of Ziegler-Natta catalysts.

2 Claims, No Drawings

DIETHERS USABLE IN THE PREPARATION OF ZIEGLER-NATTA CATALYSTS

This application is a continuation-in-part of U.S. patent application Ser. No. 07/413,409, filed Sept. 27, 1989, now abandoned.

DESCRIPTION

The present invention refers to a new class of diethers. The diethers of the invention are useful as additives for fuels (where they produce an increase in the octane number), as solvents, as a complexing agent for metal ions, and in the preparation of Ziegler-Natta catalysts.

The diethers have the general formula:

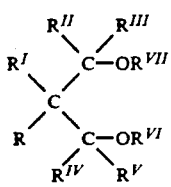

(I)

where R, $R^I$, $R^{II}$, $R^{III}$, $R^{IV}$ and $R^V$ are the same or different and are H, $C_{1-18}$ linear or branched alkyl, $C_{5-18}$ cycloalkyl, $C_{6-18}$ aryl, $C_{7-18}$ alkylaryl or $C_{7-18}$ arylalkyl radicals, provided that when R is alkyl, R is other than H or alkyl and when $R^I$ is alkyl, R is other than H or alkyl; $R^{VI}$ and $R^{VII}$ are the same or different and are $C_{1-18}$ linear or branched alkyl, $C_{5-18}$ cycloalkyl, $C_{6-18}$ aryl, or $C_{7-18}$ arylalkyl radicals; and two or more of R to $R^V$ may be bonded to form a cyclic structure having 5 to 18 carbon atoms.

The new diethers may be prepared according to various methods. For example, they may be prepared according to known etherification reactions such as the ones listed below, starting from the corresponding diols of general formula (II).

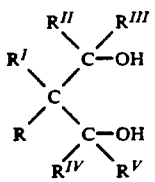

(II)

(1) Reaction of diols of formula II or the corresponding alkaline alcoholates with compounds of formula $R^{VI}$-X, $R^{VII}$-X or their mixtures (where X=Cl, Br, I, $C_6H_5$-$SO_3$, p-$CH_3C_6H_5SO_3$), wherein R, $R^I$, $R^{II}$, $R^{III}$, $R^{IV}$ and $R^V$ have the same meaning as set forth above.

(2) Reaction of diols of formula II with dialkyl sulfates of formula $R_2^{VI}SO_4$ or $R_2^{VII}SO_4$ in alkaline environment.

(3) Reaction of derivatives of general formula III, using known techniques, starting from the diols of formula II

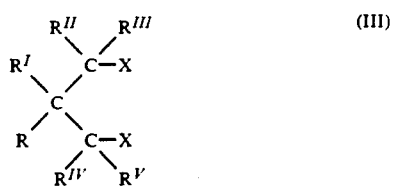

(III)

(wherein R to $R^V$ and X have the meaning as indicated above) with $R^{VI}$-OM, and $R^{VII}$-OM alcoholates, wherein M Na, K, Mg, Ca or mixtures thereof.

(4) Thermal or catalytic dehydration of mixtures of diols of general formula (II) with $R^{VI}$OH or $R^{VII}$OH alcohols or mixtures thereof.

These and other suitable methodologies are described in:

(i) Houben Weil - Methoden der Organischen Chemie Vol VI/3 Verlag ed. Stuttgard 1965.
(ii) G. W. Gokel and Coll. Synthesis 1976, 168.
(iii) G. Johns and Coll. ibid. 1976, 515.
(iv) D. Achet and Coll. ibid. 1986, 642.

The diols of general formula (II) may in turn be synthesized, for example, according to known methods such as the reduction of the corresponding diesters, dialdehydes, diketones, ketoaldehydes or dicarboxylic acids, having the general formula IV and V, and ketoesters and aldehyde esters of general formula (VI).

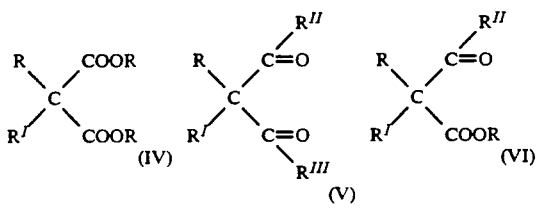

(IV) (V) (VI)

(where the radicals R, $R^I$, $R^{II}$, $R^{III}$ have the meaning as indicated above).

Examples of these methods are described in:

H. Adkins, Organic Reactions 8, 1 (1954)
N. G. Gaylord, Reduction with Complex Metal Hydrides, Interscience Publishers, N.Y., London 1956.
R. F. Nystrom, W. G. Brown, J. Am. Chem. Soc. 69, 1197 (1947).

Furthermore diols of formula II (wherein $R^{II}$, $R^{III}$, $R^{IV}$, and $R^V$ are H) may also be prepared from aldehydes of general formula (VII).

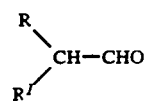

wherein R and $R^I$ have the same meaning as already specified, by action of alkaline formaldehyde according to the Cannizzaro reaction (see for example Organic Reactions Vol II, p. 94, J. While ed., N. Y., 1944).

Diols of general formula II may easily be converted into the corresponding III derivates by known methods (see Houben Weil, Methoden der Organischen Chemie, Band V/3, V/4, IX; Verlag ed. Stuttgard).

The following examples illustrate the following ethers of the invention and methods of preparing same: 2,2-diphenyl-1,3-dimethoxypropane 2,2-dibenzyl-1,3-dimethoxypropane
2,2-bis(cyclohexylmethyl)-1,3-dimethoxypropane
1,1'-bis(methoxymethyl)cyclohexane
($\pm$) 2,2'-bis(methoxymethyl)norbornane (racemic mixture).

EXAMPLE 1

Preparation of 2,2-dibenzyl-1,3-dimethoxypropane (a) Into a 500 ml flask, equipped with an agitator, refrigerant, charge funnel, thermometer and tube for the introduction of gases, were charged, under nitrogen flow, 200 ml anhydrous ethanol and 10 g (0.43 moles) Na. When the dissolution of Na was complete, 32 g (0.2 moles) diethylmalonate was introduced at once. Then the mixture was refluxed with agitation and 55 g benzyl chloride (0.42 moles) was added in 1 hour. The agitation and reflux was continued for 3 additional hours.

Most of the solvent was distilled off at reduced pressure (50 mm Hg), and the remainder hydrolized with 200 ml $H_2O$ and extracted with 2 portions of 200 ml diethyl ether. The extract was washed with water, dried over $Na_2SO_4$ and the solvent evaporated obtaining 70 g of oily product pure enough to be used as such in the next step. (Purity by gas cromatography $>95\%$).

(b) Into the same apparatus as described above in (a) were introduced, under nitrogen flow 400 ml diethyl ether and 20 g $LiAlH_4$ (0.52 moles). Then, dropwise over a period of one hour while maintaining vigorous agitation, 70 g of raw 2,2-dibenzyl malonate from (a) above was added and the mixture refluxed for 30 minutes. Excess of $LiAlH_4$ was deactivated by adding ethyl acetate (50 ml) then the reaction mixture poured into a vessel containing about 200 g of ice acidified with HCl 36% and extracted with 3 portions of 100 ml diethyl ether. The ether was evaporated and 46 g of solid raw material was produced which, when crystallized from hexane, gave 38.8 g of 2,2-dibenzyl-1,3-propandiol, with a melting point 105° C. (75.7% yield on diethyl malonate) and an elemental analysis of C=79.81% and H=7.76%. The theoretical value for $C_{17}H_{20}O_2$ is C=79.65% and H=7.86%.

(c) Into the same apparatus as described above in (a) was introduced, under nitrogen, 12.8 g (0.05 moles) 2,2-dibenzyl-1,3-propandiol, 100 ml dioxane and 15 g (0.13 moles) potassium tert-butylate. The mixture was stirred at room temperature for 30 minutes and then 18 g $CH_3I$ (0.126 moles) was added dropwise. During this procedure, the temperature rises spontaneously to 35° C. After 2 hours, an additional quantity of potassium tert-butylate (15 g, 0.13 moles) and of $CH_3I$ (18 g, 0.126 moles) was added, and the mixture refluxed for 1 hour. The reaction mass was filtered and the filtrated distilled at reduced pressure. The raw product was crystallized from ethanol giving 9 g of 2,2-dibenzyl-1,3-dimethoxy propane having a M.P. of 95° C. (63% yield on the starting material dibenzyl propandiol).

EXAMPLE 2

Preparation of 2,2-bis(cyclohexymethyl)-1,3-dimethoxypropane

Into a stainless steel autoclave provided with an anchor agitation system, 5.8 g (0.02 moles) of $(C_6H_5CH_2)_2C(CH_2OCH_3)_2$ prepared according to example 1, 100 ml n-hexane and 10 g Raney Ni washed by decanting with 3 parts 50 cc anhydrous ethanol and subsequently with 3 parts 50 cc of hexane, were introduced.

The autoclave was pressurized with 17 atm. of hydrogen and was heated to 135° C. (internal temperature) for 8 hours with agitation.

After cooling, the reaction mixture was filtered from the catalyst and vacuum evaporated, to yield 5.9 g of a colorless oil with a purity of 99%, $n^D20=1.4790$. The only compound detectable by thin layer chromatography (TLC), was 2,2-bis(cyclohexylmethyl)-1,3-dimethoxypropane.

$^1$HNMR(300 MHz, $CDCl_3$, TMS as internal standard): signals at 0.96 ppm multiplet 4 H, 1.18 ppm multiplet 12 H, 1.63 ppm multiplet 10 H, 3.15 ppm singlet 4 H, 3.27 ppm singlet 6 H.

EXAMPLE 3

Preparation of 2,2-diphenyl-1,3-dimethoxypropane (a) Preparation of 2,2-diphenyl-1,3-propandiol Into the same apparatus described in example 1 (a), 10.6 g (0.054 moles) of $(C_6H_5)$ CHCHO (Fluka), 4.03 g (0.028 moles) $K_2CO_3$, 10 cc water, 13.2 ml aqueous formaldehyde at 40% (0.176 moles) and 35 ml ethanol at 99% purity were introduced.

The mixture was stirred and refluxed for 6 hours, cooled and diluted with 300 ml of water. The precipitate thus formed was filtered, washed with water and crystallized from benzene to give 9.6 g of 2,2-diphenyl-1,3-propandiol with a m.p. 102°-104° C.

(b) Preparation of 2,2-diphenyl-1,3-dimethoxypropane

Into the same apparatus as described in (a) was charged 9.6 g 2,2-diphenyl-1,3-propandiol dissolved in 400 ml anhydrous tetrahydrofuran and stirred under nitrogen with 3.8 g NaH (55% NaH dispersed in VASELINE oil) until the production of hydrogen stops. Over a period of 20 minutes 9.6 ml $CH_3I$ was added and stirring continuously for 2 hours. Most of the THF was distilled off, then the product is diluted with water (200 ml) and extracted with two 50 ml portions of diethyl ether. The ether extract gives, by vacuum distillation, 3.5 g of 2,2-diphenyl-1,3-dimethoxypropane having a boiling point of 188° C.-190° C./20 mmHg which was unitary by TLC-chromatography and having $n^D20=1.5558$.

EXAMPLES 4 AND 5

Using the same procedure and ingredients as described above in Example 3 (a) and (b), the following compounds were prepared starting respectively from hexahydrobenzenaldehyde and norbornane-2-carboxyaldehyde.

(A) 1,1'-bis(methoxymethyl)cyclohexane boiling point 97°-98° C./20 mm Hg; $n^D20=1.4487$.

$^1$HNMR (300 MHz, $CDCl_3$, TMS as internal standard): signals at 1.36 ppm multiplet 10 H, 3.20 ppm singlet 4 H, 3.29 ppm singlet 6 H.

(B) ($\pm$) 2,2'-bis(methoxymethyl)norbornane boiling point 106°-108° C./20 mm Hg; $n^D20=1.4659$.

$^1$HNMR (300 MHz, $CDCl^3$, TMS as internal standard): signals at 0.72 ppm doublet 1 H, 1.14 ppm doublet 1 H, 1.06 ppm multiplet 1 H, 1.34 ppm multiplet 2 H, 1 51 ppm multiplet 3 H, 1.97 ppm singlet (broad) 1 H, 2.15 ppm singlet (broad) 1 H, 3.06 ppm system AB 1 H, 3.14 ppm system AB 1 H, 3.33 ppm system AB 1 H, 3 36 ppm system AB 1 H, 3.29 ppm multiplet 6 H.

Polymerization of Propylene

EXAMPLE 6

Into a 500 ml reactor, equipped with a filter disk on the bottom, 225 ml $TiCl_4$ was introduced at 0° C. and with stirring over a period of 15 minutes, 10.1 g (54 mmols) $MgCl_2 \cdot 2C_2H_5OH$ in microspherical form prepared according to example 1 of U.S. Pat. No. 4,469,648 was added.

Upon completion of the addition, the temperature was raised to 40° C. and 9 mmols diisobutyl phthalate was introduced. The temperature was then raised to 100° C. over 1 hour and the mixture was reacted for 2 hours. The excess $TiCl_4$ was then removed by filtration. 200 ml $TiCl_4$ was then added and the contents heated at 120° C. for 1 hour while stirring. The mixture was filtered and the solid washed with n-heptane at 60° until no chlorine ions were in the filtrate.

In a 2000 ml stainless steel autoclave equipped with an anchor stirrer there was introduced, at 25° C. under propylene flow, 1000 ml n-heptane, 5 mmols $Al(C_2H_5)_3$, 30 mg of catalyst component prepared above and 1 mmol of 2,2-bis(methylcyclohexyl)-1,3-dimethoxypropane.

The autoclave was closed. After the pressure had been set at 1 atm, 0.2 atm hydrogen was introduced and the contents heated at 70° C. while propylene was fed in up to a total pressure of 7 atm.

The polymerization was carried out for 2 hours. During that period monomer feeding was continued. The polymer was isolated by filtration at the end of the reaction period, and vacuum dried. The remaining portion of polymer in the filtrate was precipitated with methanol, vacuum dried and considered in determining the total residue extractable with n-heptane. 5000 g of polypropylene was obtained with an isotactic index of 92.7% and intrinsic viscosity of 1.30.

Other features, advantages and embodiments of the invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

What is claimed is:

1. A diether compound of formula:

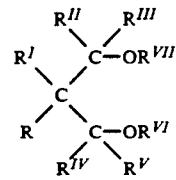

where $R$, $R^I$, $R^{II}$, $R^{III}$, $R^{IV}$ and $R^V$ are the same or different and are H, $C_{1-18}$ linear or branched alkyl, $C_{5-18}$ cycloalkyl, $C_{6-18}$ aryl, $C_{7-18}$ alkylaryl or $C_{7-18}$ arylalkyl radicals, provided that when R is H or alkyl, $R^I$ is other than H or alkyl and when $R^I$ is H or alkyl, R is other than H or alkyl; $R^{VI}$ and $R^{VII}$ are the same or different and are $C_{1-18}$ linear or branched alkyl, $C_{5-18}$ cycloalkyl, $C_{6-18}$ aryl, or $C_{7-18}$ arylalkyl radicals; and two or more of R to $R_V$ may be bonded to form a cyclic structure having 5 to 18 carbon atoms.

2. The diether compound according to claim 1 selected from the group consisting of 2,2-diphenyl-1,3-dimethoxypropane, 2,2-dibenzyl-1,3-dimethoxypropane, 2,2-bis(cyclohexylmethyl) 1,3-dimethoxypropane, 1,3-bis(methoxymethyl)cyclohexane and 2,2'-bis(methoxymethyl)norbornane.

* * * * *

UNITED STATES PATENT AND TRADEMARK OFFICE
CERTIFICATE OF CORRECTION

PATENT NO. : 5,095,153
DATED : March 10, 1992
INVENTOR(S) : Agnes et al

It is certified that error appears in the above-identified patent and that said Letters Patent is hereby corrected as shown below:

On the title page,
Abstract, line 9, change "$C_6$" to --$C_{6-18}$--.

Abstract, line 12, change "$R^{VIII}$" to $R^{VII}$--.

Col. 1, line 31, change the second occurrence of "R" thereof to --$R^I$--.

Col. 1, line 58, after p-$CH_3C_6H_5SO_3$" insert --,$CH_3SO_3$--.

Col. 2, next to last formula thereof, insert --(VII)--.

Col. 4, line 20, change "$(C_6H_5)CHCHO$" to --$(C_6H_5)_2CHCHO$--.

Col. 4, line 63-64, change "1 51" to --1.51.

Col. 4, line 66, change "3 36" to --3.36--.

Col. 6, line 29, change "$R_V$" to --$R^V$--.

Signed and Sealed this

Second Day of November, 1993

Attest:

BRUCE LEHMAN

*Attesting Officer*  *Commissioner of Patents and Trademarks*